US006491956B2

(12) United States Patent
Heo et al.

(10) Patent No.: US 6,491,956 B2
(45) Date of Patent: Dec. 10, 2002

(54) FOOD CONTAINING ACTIVE STRAINS FOR INHIBITING INFECTION AND TREATING GASTRITIS, GASTRIC AND DUODENAL ULCERS

(75) Inventors: Cheol Seong Heo, Chunan (KR); Jeong Jun Lee, Suwon (KR); Young Jin Baek, Seoul (KR); Hyung Soo Kim, Granger, IN (US)

(73) Assignee: Korea Yakult Co. Ltd., Seoul (KR)

( * ) Notice: Subject to any disclaimer, the term of this patent is extended or adjusted under 35 U.S.C. 154(b) by 0 days.

(21) Appl. No.: 09/974,461

(22) Filed: Oct. 10, 2001

(65) Prior Publication Data

US 2002/0037341 A1 Mar. 28, 2002

Related U.S. Application Data

(63) Continuation-in-part of application No. 09/498,668, filed on Feb. 7, 2000, now Pat. No. 6,329,002.

(30) Foreign Application Priority Data

Feb. 8, 1999 (KR) .............................................. 99-04234
Sep. 20, 1999 (KR) .............................................. 99-40387

(51) Int. Cl.[7] .............................................. A01N 63/00
(52) U.S. Cl. .......................... 426/71; 426/61; 426/583; 424/93.4
(58) Field of Search .............................. 426/61, 42, 43, 426/2, 583, 71; 424/93.1, 93.45, 93.4

(56) References Cited

U.S. PATENT DOCUMENTS 5,494,664 A * 2/1996 Brassart et al. ............. 424/93.4
6,329,002 B1 * 12/2001 Kim et al. ..................... 426/71

FOREIGN PATENT DOCUMENTS

EP 0 877 032 * 11/1998
JP 4275232 * 9/1992

OTHER PUBLICATIONS

Lee et al., "Effect of Bifidobacterim longum HY8001 administration . . . ", Korean Journal of Applied Microb. & Biotech., 27(4): 267–272, (abstract), Jan. 1999.*

* cited by examiner

*Primary Examiner*—Keith Hendricks
(74) *Attorney, Agent, or Firm*—Alfred D. Lobo (57) ABSTRACT

Live strains of *Lactobacillus acidophilus* HY2177 and *Lactobacillus casei* HY2743 maintained in nutritious foods, such as yogurt, imbue them with prophylactic and/or therapeutic properties. Such foods are beneficial in the prevention and/or treatment of gastritis, duodenal and gastric ulcers caused by infection from *Helicobacter pylori* (also referred to as *H. pylori*). The properties of these bacteria are boosted by the addition of egg yolk containing antibodies specific to *H. pylori* antigen derived from "fractionated *H. pylori*" and may be administered as active strains alone in a food supplement, or the active strains may be combined with *H. pylori*-antibodies (IgY).

18 Claims, 5 Drawing Sheets

FOOD CONTAINING ACTIVE STRAINS FOR INHIBITING INFECTION AND TREATING GASTRITIS, GASTRIC AND DUODENAL ULCERS

CROSS-REFERENCE TO RELATED APPLICATION

This application is a continuation-in-part application of Ser. No. 09/498,668 filed on Feb. 7, 2000 now U.S. Pat. No. 6,329,002.

FIELD OF THE INVENTION

A nutritional formulation in which non-toxic (to humans) bacteria thrive, is used to prevent and treat gastric disorders associated with *Helicobacter pylori* (also referred to as *H. pylori*) which are believed to be attacked by the non-toxic bacteria. Only particular strains of non-toxic comestible bacteria, when ingested by humans are effective against *H. pylori*. Optionally and preferably, the prophylactic and/or therapeutic effects of the comestible bacteria are boosted with egg yolk containing immunoglubins (antibodies) specific to *H. pylori* antigen (also referred to as "*H. pylori*-antibodies").

BACKGROUND OF INVENTION

Much has been published regarding *H. pylori* which inhabits the human gastric mucosa. It is a gram-negative spiral rod-shaped bacterium having an outer membrane with four to six polar flagella which are sheathed and have bulbous ends; each *H. pylori* bacterium is about 0.85 μm (micrometer) in diameter with an average length of 2.9 μm. Known pathogenic (disease) factors of *H. pylori* are (i) urease (urea aminohydrolase) which is produced by the bacteria to allow it to thrive in a strong acid environment in the range from pH 1–3, (ii) flagella which provide the bacteria with mobility, and (iii) a protein-aceous outer membrane of the cells which membrane helps the cells to stick to the gastric mucosal cells. Survival of *H. pylori* relies upon creation of a relatively non-acidic microenvironment in the vicinity of the bacteria, and a relatively basic microenvironment is provided by the enzyme urease; the more basic the better, and the closer to neutral pH, the more difficult it is for the *H. pylori* to thrive. The ability to command a near-neutral microenvironment is an essential property of bacteria which effectively prevent and treat gastric disorders.

A result of interaction of *H. pylori* on the mucous membrane is the stimulation of numerous cytokines. The predominant immune response to infection is the production of interleukin-8 (IL-8). IL-8-induced neutrophils or macrophages are a direct cause of gastritis. To date, treatment to subdue secretion of gastric acid, for example with $H_2$ isolator, is deemed unsatisfactory over the long term due to recrudescence which is now countered with medicines which act directly on the *H. pylori*. Presently, trends in the fight against infection by *H. pylori* may be categorized as follows: (a) development of antibiotics showing a direct effect against *H. pylori*, (b) development of vaccines for *H. pylori*, and (c) using anti-*H. pylori* antibodies which allow the live *H. pylori* to be terminated. For prophylaxis, (b) and (c) are preferred.

Figure 1:
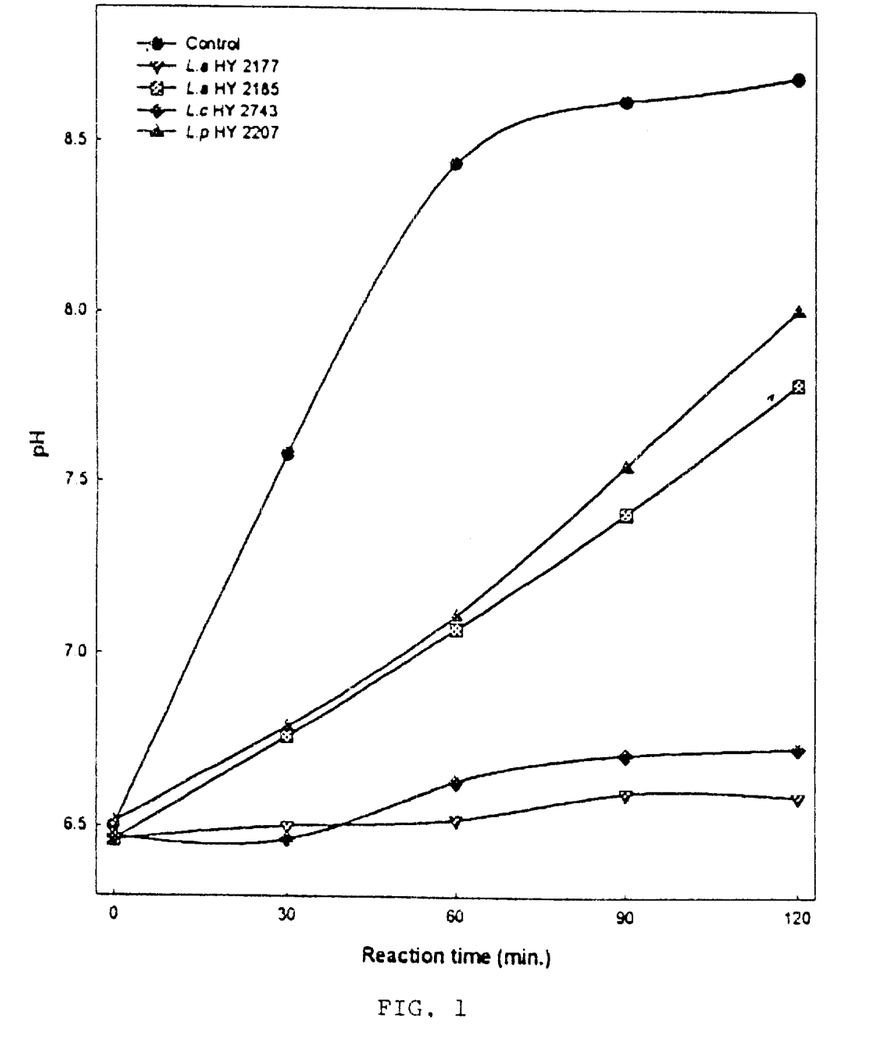
FIG. 1 shows five curves in a graph, one of which is for the control, each curve showing the pH measured as a function of time as a result of the effect of four strains of bacteria, two for strains of the same species *L. acidophilus*, the strains having similar in vitro activity; and one curve each for *L. casei* HY2743 and *L. plantarum* HY2207, different species having similar in vitro activity.

Bhatia et al in *J. Clin. Microbiol.* 27: 2328–2330, 1989, disclosed that *L. acidophilus* could inhibit the growth of *H. pylori* in vitro, and that this effect was due to lactic acid production. Midolo et al in *J. Appl. Bacteriol.* 79:475–479, 1995, disclosed that *L. casei, L. bulgaticus, Pediococccus pentosaceus* and *Bifidobacterium bifidus* could inhibit the growth of *H. pylori* in vitro, and that this effect was due to organic acids produced by these bacteria. However, as stated in European Patent Application EP 0 877 032 A1 to Kodama et al (hereafter, "the '032 application"), one cannot expect experiments conducted in vitro to be replicated in the stomach. An attempt to use *Lactobacillus salivarius* as a probiotic to inhibit growth of *H. pylori* is reported by Aiba et al in *The Meeting of the 30th Japan Germ-free Animal Gnotobiology Society*, Program and Abstracts, pp 22, Requested Title 18, "New Attempt for Inhibiting *H. pylori*" (January 1997). They also used anti-*H. pylori* antibodies in the yolks of eggs of hens immunized with formalin-lidlled, whole *H. pylori* cells. In germ-free mice, the effectiveness of the *L. salivarius* was 2 to 3 orders of magnitude greater than that of the antibodies; effectiveness in the environment of the stomach of a mammal such as a normal mouse, or in the pH 1–3 of a human, was not investigated. Though the particular strain of *L. salivarius* was not identified, there is no reason to believe that any lactic acid bacteria will be comparably effective even in a germ-free mouse; data presented below in FIG. 1 indicate that several species of Lactobacillus show high in vitro activity, but are not as effective in vivo as others with comparably high in vitro activity. Moreover, as also shown in FIG. 1, strains which show desirably high in vitro activity, e.g. *L. casei* HY2743 and *L. plantarum* HY2207 are found to be far from equally effective in vivo.

In the prior art there are taught many immunization schedules under which growth of anti-*H. pylori* antibodies can be stimulated, most relevant among which are the disclosures of Japanese Patent Application Kokai No. 4-275232 to Takahashi et al, which discloses antibodies obtained in eggs of hens immunized against *H. pylori* whole cells as an antigen; and, the disclosure of the '032 application which discloses antibodies obtained in eggs of hens immunized against (i) flagella of *H. pylori* separated from the rest of the cells; and (ii) urease of *H. pylori* separated from the rest of the cells, these being pathogenic factors associated with *H. pylori*. Antibodies obtained from either (i) or (ii), by themselves, had no noticeable effect on the number of cells in the stomach of five mice; however, (i) and (ii) in combination eliminated the *H. pylori* cells from the stomachs of 5 out of 5 mice. (see Table 2 in the '032 application).

Takahashi et al teach the use of a solution of shattered or comminuted *H. pylori* as antigen, but the beneficial effects are relatively small because the solution additionally contains many other different proteins which appear to dilute, if not diminish or negate, the ability of the antigen to generate effective antibodies.

Furthermore, Kodama et al teach that either the anti-urease antibodies or the anti-flagella antibodies, or both together, may be used in combination with at least one organism selected from the group consisting of lactic acid bacteria, Enterococci, yeasts and Bacillus to inhibit the growth of *H. pylori* in the stomach, teaching that the presence of any live organism unexpectedly enhances the effectiveness of the antibodies, though the live organism, by itself, was ineffective in the environment of the stomach. In particular, Kodama states that *L. acidophilus, L. casei, L. bulgaricus, Pediococcus pentosaceus* and *Bifidobacterium bifidus* were all reported to inhibit growth of *H. pylori* in vitro purportedly due to organic acids produced by these bacteria, but such effectiveness was of no help to assess the effect in the stomach. Evidence of the synergistic effect of anti-urease antibodies and *Lactobacillus acidophilus* administered in combination orally to *H. pylori*-infected mice is presented in Table 3 of EP '032. Note however, that only one-half of the population of *L. acidophilus* is found after 14 days. Without considering the propriety of extrapolating those results to all live organisms tested, it is evident from results presented in Table 3 that one particular strain of *L. acidophilus* showed a synergistic effect with *H. pylori*-urease. However, one skilled in the art is unable, without undue experimentation, to reproduce the effect reported, because it is not reasonably possible to find the single strain among all the known strains of *L. acidophilus* which produces the synergistic result.

Confirmation of the ineffectiveness of the live organism, by itself, is stated as follows: "*L. acidophilus* alone was almost the same as that of the control group, and there was no significant difference between the two groups, as shown in Table 3. Also, gastritis conditions were observed and *L. acidophilus* had no efficacy on suppressing gastritis." (see page 10, lines 49–52). The tests were performed on hairless mice (NS:Hr/ICR) having a high sensitivity to *H. pylori* infection. Such mice do not have the normal flora found in a BALB/c mouse which provides a better comparison with a human stomach.

Contrary to Kodama's teaching, we found that to get the beneficial effects of a bacteria in vivo in the stomach, it is critical that we use a live bacteria which by itself is highly effective in vitro against *H. pylori*- and to boost its effect, to use antibodies produced by antigens of fractionated *H. pylori*. The term "fractionated *H. pylori*" refers to particular portions of *H. pylori* which portions are separated from the remainder of the cells; the separated portions are as follows: (i) urease; (ii) the outer membrane and (iii) the flagella; the remainder of the cells is discarded. Since it is not practical to conduct a very large number of in vivo experiments with *H. pylori*-infected mice using strains of various bacteria, we chose to use a combination of the three strains found after screening a limited number of strains set forth in Table 1 below. It is recognized that there may be S one or more specific strains of *L. acidophilus*, not suggested in the '032 application, any one of which, by itself, may be effective against *H. pylori* not only in vivo but also in vitro; they chose to use a strain which was effective in neither.

It is now evident that, in the prior art, the problem of attacking the *H. pylori* in a stomach relied upon the *H. pylori*-antibodies collected from one or more constituents of fractionated *H. pylori*; or, in combination with a bacteria such as *L. acidophilus* used in the '032 application, or any other bacteria which by itself had no noticeable effect in the environment of a stomach. The invention described hereunder derives from the realization that only particular strains of a genus have the ability, when ingested by humans, to survive the environment of the stomach for long enough to find the relatively less acidic zones around *H. pylori* attached in the stomach's lining, and to excrete bacteriocins which would attack the *H. pylori*. A search was made for those bacteria which could be relied upon to provide a major portion of the desired attack, their effectiveness being supplemented with conventionally derived *H. pylori*-antibodies.

Further, the prior art typically obtained egg yolk powder by freeze-drying an aqueous solution, and was unconcerned with formulating a commercially marketable food fortified with egg yolk powder containing *H. pylori*-antibodies; this led to a lack of concern to stabilize the antibodies during spray-drying of egg yolk solution to make the powder, spray-drying to sterilize being the preferred commercial method of production of egg yolk powder. Sterilization requires spray-drying at a temperature of at least 65° C. at which temperature the antibodies are unstable. The prior art did not provide a solution to the problem of finding a comestible, non-toxic water-soluble food ingredient which is able to stabilize the antibodies in the egg yolk solution at a pH and temperature which would not deleteriously affect the antibodies.

Despite the development of several medicines for the treatment of disorders due to *H. pylori*, the prior art has failed to suggest any logical basis for selecting an active strain of non-toxic, live bacteria for such treatment, except trial and error. By "active strain" is meant a non-toxic strain of live bacteria which effectively kills or inhibits the growth of *H. pylori* grown as a lawn in a growth-conducive anaerobic or microaerophilic environment, on a medium in vitro, in an amount sufficient to provide a zone free of *H. pylori*, which zone is visually observable with the naked eye. Particularly because it was found that certain strains of lactobacillus were effective for our purpose, as set forth in Ser. No. 09/498,668, now U.S. Pat. No. 6,329,002 we chose to study additional strains to find specific strains which produced the appropriate *H. pylori*-specific bacteriocins, and specifically those strains which could be delivered in food routinely consumed by humans.

SUMMARY OF THE INVENTION

A natural or synthetic food is supplemented with particular strains of live bacteria which by themselves are effective against *Helicobacter pyloti* (also referred to as *H. pylori*) not only in vitro but in vivo. The effectiveness of such bacteria is strain-specific, that is, a specific strain of a species may be effective while other strains of that same species are not. Effectiveness of "active strains" identified herein may be preserved and/or enhanced with egg yolk containing antibodies specific to *H. pylori* antigens, so that consuming the food will prevent and/or treat gastritis, and/or gastric and duodenal ulcers.

It has been discovered that specific strains of non-toxic (to humans) live bacteria, by themselves, when maintained as "active strains" in comestible foods, such as yogurt and other bacteria-tolerant foods which may contain other living organisms, have the unique ability to imbue such foods with prophylactic and/or therapeutic properties because, it is hypothesized, active strains produce bacteriocins which directly attack *H. pylori*; they also compete for adhesion sites and produce organic acids which create a hostile environment for the *H. pylori*. In the genus of lactic acid bacteria, only the strains *Lactobacillus acidophilus* 1–2 HY2177, and *Lactobacillus casei* HY2743 (together referred to herein as "active lactic acid bacteria strains" or "active strains" for brevity) have been found either to minimize the growth of, or to destroy *H. pylori* not only in vitro but also in vivo in the environment of a stomach, provided each strain is used, either individually or in combination, in an effective dosage amount. Their effectiveness is measured by the ability of these active lactic acid bacteria strains (i) to inhibit the attachment of *H. pylori* to gastric mucosal cells of the stomach's mucous membrane; (ii) to inhibit the production of urease substantially completely, indicated by no significant increase in pH, and (iii) to inhibit the production of Interleukin-8 (IL-8) by as much as about 90%, indicated by an ELISA analysis.

It is therefore a general object of this invention to provide a food for general human consumption, comprising a food stored at a temperature in the range from about −45° C. but no more than 45° C. and effective to inhibit and/or prevent the growth of *H. pylori* in a human stomach; the food is fortified with an active strain selected from the group consisting of *Lactobacillus acidophilus* HY2177 and *Lactobacillus casei* HY2743, preferably a combination of both, optionally in combination with antibodies obtained in the yolk of an egg of a hen immunized against a pathogenic factor selected from the group consisting of fractionated *H. pylori* and urease of *H. pylori*. "Fractionated *H. pylori*" consists essentially of a pathogenic factor selected from the group consisting of *H. pylori*-urease (hereafter referred to only as "urease"), flagella of *H. pylori* and outer membrane of *H. pylori* separated from the rest of the mass of *H. pylori* cells. Portions (ii) and (ii) are typically used together (referred to as "flagella/outer membrane") to avoid the effort of separating them, were each to be used individually. Urease, though not an integral portion of the *H. pylori* cells is referred to as a constituent of fractionated *H. pylori* because it is derived from, and separated from the comminuted cells.

It is a specific object of this invention to provide an improved food selected from the group consisting of a conventional food of lactic acid bacterial origin and a non-conventional food, in combination with an effective dosage amount of an active strain selected from the group consisting of *Lactobacillus acidophilus* HY2177 and *Lactobacillus casei* HY2743, the conventional food being selected from the group consisting of yogurt, buttermilk cream cheese and ice cream, and the non-conventional food being a nutritional yogurt drink. The useful concentration of active lactic acid bacteria strain(s) in the food is in the range from about $1\times10^8$ cfu/ml to about $1\times10^{10}$ cfu/ml, preferably in the range from $5\times10^8$ cfu/ml to about $5\times10^{10}$ cfu/ml, and optimally about $1\times10^9$ cfu/ml in a unit serving. The useful concentration of *H. pylori*-antibodies in egg yolk is in the range from 50 mg to about 250 mg per unit serving, typically in yogurt. The egg yolk is typically used in a fortified food in the range from about 0.05% to about 4% by weight of the food, preferably in the range from 0.5 to 2%, so that at 2% the food contains less than 125 mg of antibodies.

It is another specific object of this invention to provide a food or food supplement containing an effective dosage amount of at least one of *L. acidophilus* HY2177 and *L. casei* HY2743, which over a course of treatment, effectively (i) inhibits the attachment of *H. pylori* to gastric mucosal cells of the stomach's mucous membrane; (ii) inhibits the production of urease substantially completely, indicated by no significant increase in pH, and (iii) inhibits the production of Interleukin-8 (IL-8) by as much as about 90%, indicated by an ELISA analysis.

It is another general object of this invention to provide a method of preventing and/or treating disorders associated with infection by *H. pylori*, the method comprising administering to a human a nutritional food in combination with an effective dosage amount of one or more of the active strains identified immediately hereinabove, in plural successive unit servings, each unit serving spaced apart from a prior one by a period in the range from 1 hour to 3 days; and, preferably to do so in combination with egg yolk powder containing *H. pylori*-antibodies derived from one or more of the aforespecified pathogenic factors, most preferably both in combination, wherein the antibodies have been stabilized with from about 5% to about 20% by weight of a water-soluble simple sugar. By a "unit serving" we refer to a conventional individual serving for the particular food being fortified; for example, for yogurt, a typical unit serving is 8 fl oz (fluid ounces) or about 450 ml, though it may range from 4 fl oz to 12 fl oz (250 ml to 950 ml). The term "simple sugar" refers to a carbohydrate containing an α-hydroxy aldehyde or an α-keto primary alcohol, preferably sucrose, fructose, lactose, glucose, dextrose and the like.

It is another specific object of this invention to provide a novel adjuvant which is more effective to potentiate an immune response to *H. pylori* antigens than conventionally used Freund's adjuvant (complete or incomplete) and which not only produces more antibodies than with conventional adjuvants, but also produces more than 75% of the antibodies in the yolk of a hen immunized with an antigen of fractionated *H. pylori* in the novel adjuvant.

BRIEF DESCRIPTION OF THE DRAWING

The foregoing and additional objects and advantages of the invention will best be understood by reference to the following detailed description, accompanied with schematic illustrations of preferred embodiments of the invention, in which illustrations like reference numerals refer to like elements, and in which.

DETAILED DESCRIPTION OF PREFERRED EMBODIMENTS

Screening of non-toxic bacteria for effectiveness against *H. pylori*:

A test procedure for finding bacteria which, by themselves, are effective in vitro is as follows—*H. pylori* cells in a concentration of $10^6$ cfu/ml) were inoculated into skim milk, made with distilled water and 12% non-fat milk solids (NFMS), and incubated at 37° C. for 24 hours as inoculants. Several kinds of lactic acid bacteria cultures were similarly cultured for 2 days and filtered with a 0.45 μm filter to provide a test culture having about the same concentration (cfu/ml) of cells as the *H. pylori* incubated for 24 hr. Strains of bacteria which form a substantial inhibition ring are then identified. By "substantial inhibition" is meant that the area of the annular zone of inhibition is at least as great as the area of a circle into which the test culture is deposited. Of the many strains tested (see Table 1) the following four were found to be active strains which provide substantial inhibition: L. acidophilus HY2177 (patent file # 00-07982, applicant: Korea Culture Collection, application number: KFCC 11142); L. acidophilus HY2185 (culture not deposited); L. casei HY2743 (patent file #00-7982 applicant: Korea Culture Collection, application number: KFCC 11143); and L. plantarum HY2207 (culture not deposited).

Four cylinders, each 8.1 mm in diameter, are set on a plate and 25 ml Brucella agar is poured around the peripheries of the cylinders and congealed. 170 μl (microliters) of a suspension of H. pylori ($10^9$ cfu/ml) was overlaid on the surface of the congealed agar. The cylinders were removed and the plate cultivated in a microaerophilic atmosphere at 37° C. to produce a lawn of H. pylori around four 8.1 mm diameter circles left by the removed cylinders. Then 170 μl of a liquid culture of lactic acid bacteria (cultivated for two days) is deposited within each circle. After cultivating the bacteria on the plate for 24–48 hr at 37° C., the inhibition zone is recognized as the diameter of the zone around the periphery of each circle. A visible growth of H. pylori at the circumference of each circle is evidence of no visible inhibition, that is, the diameter of the circle is 8.1 mm; and, the larger the diameter of the inhibition zone, the more effective is the strain of bacillus tested.

TABLE 1

| Strain | Average, mm |
| --- | --- |
| L. acidophilus HY2105 | 9.5 ± 0.3 |
| L. acidophilus HY2177 | 18.9 ± 1.5 |
| L. acidophilus HY2109 | 8.9 ± 0.6 |
| L. acidophilus HY2185 | 15.6 ± 1.7 |
| L. acidophilus HY2122 | 8.1 ± 1.1 |
| L. bulgaricus HY2345 | 9.2 ± 0.7 |
| L. bulgaricus HY2340 | 8.7 ± 1.2 |
| L. casei HY2726 | 9.8 ± 0.5 |
| L. casei HY2772 | 9.2 ± 0.3 |
| L. casei HY2743 | 14.2 ± 1.0 |
| L. gasseri HY2992 | 9.8 ± 0.2 |
| L. cryspatus HY2830 | 8.8 ± 0.4 |
| L. brevis HY2505 | 9.3 ± 0.5 |
| L. plantarum HY2207 | 13.8 ± 0.9 |
| L. plantarum HY2255 | 8.2 ± 0.6 | and several others tested showed no inhibition effect at all.

In addition to commonly ingested foods, the bacteria and/or antibodies may be delivered in an oral liquid medicine to a patient suffering from duodenal and gastric ulcers, or to one recovering from a stomach or duodenum operation, or as a food supplement to one who simply has an upset stomach. Humans who have been consuming (a) one or more of the identified active strains in an amount in the range stated above; or, (b) the combination of one or more of the identified active strains in the stated amount, with yogurt in the stated amount, have shown no sign of gastritis or of gastric or duodenal ulcers. For example, a unit serving of 100 ml of yogurt contains from 0.5 gm to about 2 gm of egg yolk containing antibodies in the range from 10 mg to 40 mg. The results for the treatment of humans with ulcers are not currently available as the tests are in progress.

Antibodies obtained from fractionated H. pylori in combination with one or more of the foregoing active strains of bacteria produce additive results in efficacy against H. pylori, and in some instances produce unexpectedly enhanced results. The beneficial effects of the bacteria and/or the antibodies are best experienced when combined with yogurt, ice cream, infants' formula, and foods after they have been formulated, so as not to be subjected to a temperature which will inactivate the bacteria.

Foods, fortified with the live bacteria and/or egg yolk, may be any conventional food for humans, but is preferably of lactic acid bacterial origin, such as yogurt, buttermilk, cream cheese and ice cream. The fortified food may also be a non-conventional food produced from natural products by physical and chemical modification, for example, an acceptable alternative for yogurt which mimics the characteristic milky taste and mouth-feel of drinkable yogurt while providing supplemental nutrition in the form of protein, carbohydrate, fat, vitamins and minerals in each serving. One particular example of a non-conventional food is liquid or frozen yogurt prepared by combining sources of fat and milk-derived solids with a relatively undenatured whey protein concentrate to form a mixture having no more than 2 parts casein to 1 part whey protein, as described more filly in U.S. Pat. No. 4,110,476, the disclosure of which is incorporated by reference thereto as if fully set forth herein. Another particular example of a non-conventional food is a protein-containing nutritional supplement containing from 1 to 10% by weight of whey protein isolate, at least one source of carbohydrate, vitamins, trace minerals and ultra trace minerals, as described more fully in U.S. Pat. No. 5,641,531, the disclosure of which is incorporated by reference thereto as if fully set forth herein. Still another is simply as a food supplement.

Manufacture of Antibody:

H. pylori-antibodies are obtained in the yolks of eggs from hens vaccinated with either one or more of the constituents of fractionated H. pylori. The hens are white Leghorns, 30–50 weeks old, vaccinated by muscle shot or injection. Antigens of fractionated H. pylori were obtained from H. pylori ATCC43504 and also from infected patients (KS 51). In the tests described hereunder, the KS 51 was used because they were easier to cultivate.

A specific oily vaccination-promotive adjuvant is used rather than the Freund's complete or incomplete adjuvant of the prior art, mainly because the novel oily adjuvant provides better production of antibodies on a large scale, concentrates the antibodies in the egg yolk, both of which make production of the antibodies unexpectedly economical. This novel adjuvant consists essentially of an emulsifier mixed with a mineral oil such as Drakeol®. The emulsifier was produced by mixing the mineral oil with a stabilizing detergent. By "stabilizing detergent" is meant a detergent that allows the components of the emulsion to remain as a stable emulsion. Such detergents include polysorbate, 80 (Tween) (Sorbitan-mono-9-octadecenoate-poly(oxy-1,2-ethanediyl; manufactured by ICI Americas, Wilmington, Del.) Tween 40, Tween 20, Tween 60, Tween 85, Zwittergent 3-12, Teepol HIB7, and Span 85. These detergents are usually provided in an amount of approximately 0.05 to 0.5%, preferably at about 0.2%. Most preferred is a mixture of Span® 85 and Tween® 85 in a ratio in the range from about 40:60 to about 60:40, most preferred being 54:46. A mixture of Drakeol®, emulsifier, and antigen in a ratio in the range from about 5:1:4 to about 13:1:12, optimally 9:1:8, respectively, was emulsified.

Hens are vaccinated four times, each successive vaccination spaced apart from a prior one by an interval of 2 weeks, until a sufficiently high level of desired antibodies is obtained. The characteristic value of antibodies transferred to an egg was measured by the Enzyme Immune Absorption method, or by the Microtiter method.

Whole egg powder and egg yolk aqueous protein powder, each containing antibodies, and purified antibodies obtained therefrom, are manufactured by monitoring the changes of antibody value by Microtiter after vaccinations of hens at 1 week intervals, and taking an egg when it shows a sufficiently high (increased) value of antibody.

Production of Powder From Aqueous Egg Yolks Containing Antibodies:

The separation of antibodies may be done by any conventional antibody-separating method, it being preferred to separate the egg yolks from the albumen, and homogenizing them in a Homo-Mixer in about a four-fold volume of distilled water. The antibody value of the mixture, determined by Microtiter in the range from 30 to 200, typically about 100. Then 2 mg of lambda carrageenan is added for each ml of homogenized mixture and shaken before allowing the mixture to stand for 30 min. Thereafter the mixture is centrifuged at 10,000 g for 10 min. The supernatant liquid is filtered through filter paper and the filtrate is concentrated to one-tenth of its volume by removing 90% of the liquid as permeate through an ultra-filtration membrane which allows only those molecules having a molecular weight lower than 30,000 Daltons to pass through the membrane. The concentrate is then freeze dried to yield a powder of water-soluble proteins which contain desired antibodies.

Production of Purified Antibodies From Egg Yolks Powder:

The freeze-dried powder obtained above was dissolved in distilled water and passed through an ion-exchange column in which the antibodies are separated from the egg yolk. The antibodies are then eluted from the column to provide a solution of purified antibodies. Alternatively, purified antibodies may be obtained from aqueous egg yolk protein by any other conventional method such as liquid chromatography, affinity chromatography, etc. The purified antibodies are obtained by vacuum drying the solution of purified antibodies.

Selection of Lactic Acid Bacteria According to their Effect on *H. pylori*:

The selection process yielded the above-identified active strains of bacteria, which were cultivated for use either individually or in combination, one with another. For brevity, the strains are hereafter referred to as HY2177; HY2185; HY2743; and HY2207. Upon further testing as described below only HY2177 and HY2743 were chosen.

In the following illustrative examples all "parts" refer to "parts by weight" unless stated otherwise.

EXAMPLE 1

A. Preparation of Flagella/Outer-membrane Antigen

A broth of *H. pylori* (KS 51) obtained from a patient was cultivated in a microaerophilic atmosphere (3%–5% oxygen, 10% carbon dioxide, remainder nitrogen) at 37° C. for 2 days using Brucella medium containing 5% fetal bovine serum (FBS), and the culture concentrated by centrifuging it at 4000 g for 20 min. This concentrate of cultured cells was collected and suspended in phosphate physiological salt buffer. The concentrate was disintegrated (by sonication) and centrifuged at 10,000 g for 20 minutes so as to discard the larger particles. The obtained supernatant layer was then centrifuged at 100,000 g for 30 mins to separate a pellet of wanted flagella and outer membrane from a supernatant layer which contains the urease.

B. Preparation of Urease Antigen

A concentrate of cells cultured, collected, sonicated and suspended in phosphate physiological salt buffer in a manner described immediately hereinabove was flowed through a DEAE-Sephacel anion-exchange column, washed with phosphate physiological salt buffer (pH 6.8) of 20 nM and then eluted with a 1.0 M NaCl solution (density distribution method). Samples adsorbed in successive sections of the column are collected. The absorption of each section was measured at a wavelength of 280 nm (nanometers) and the sample with the highest absorption was verified by the urease test method. This sample was dialyzed with the same buffering solution, concentrated using an ultra filter membrane, and the filtered concentrate used as an antigen.

EXAMPLE 2

Manufacture of *H. pylori*-antibodies in Eggs

The flagella is not separated from outer membrane in Example 1 above, because separation is difficult; it is also needlessly expensive to separate proteins of similar molecular mass. Flagella/outer membrane antigen obtained in Example 1 was mixed with the novel adjuvant and shot by intramuscular injection into the pectoral muscles of white leghorn hens 40 weeks old, at intervals of 2 weeks until a sufficiently high level of antibody was obtained. The concentration of flagella/outer membrane in the adjuvant is in the range from 60 mg/ml to 200 mg/ml typically about 100 mg/ml; and 1 ml is injected each time.

The characteristic value of antibody transferred into an egg was measured using Microtiter method as follows.

The aqueous protein fraction of egg yolk containing antibodies obtained as described above from eggs collected every 2 weeks, is mixed with an aqueous solution of lambda carrageenan (0.15% w/v) so that there is 1 g of lambda carrageenan in 9 ml of the mixture. The mixture is left at room temperature (20° C.) for 30 minutes, and then centrifuged at 10,000 g for 10 min to provide a supernatant solution. This solution was diluted with saline phosphate buffered saline buffer (PBS, pH 7.4) to provide numerous samples at various dilutions, represented as $2^n$ diluted test samples. 50 $\mu$l (microliter, that is, $10^{-6}$ liter) of each test sample is mixed with an equal volume (50 $\mu$l) of sonicated bacteria and smeared on a microplate which is maintained at 37° C. for 24 hours, after which each test was checked for agglutination. The value of antibody agglutination was expressed as the reciprocal of the maximum dilution ratio of the sample, at which the agglutination is displayed.

Manufacture of Aqueous Protein Powder of Egg Yolk:

After separation from the eggs, yolks having an antibody agglutination value of 640 or higher are homogenized in a Homo-mixer, and mixed so as to make up 500 ml of solution with 400 ml of a lambda carrageenan (2 mg/ml) solution. After leaving this solution at the room temperature for 30 minutes, the egg yolk fatty protein was separated by precipitation using the centrifugal separation (10,000 g, 10 minutes). By filtering the supernatant through filter paper, concentrating by 10 times with an ultra-filter membrane which removes that fraction which is higher than molecular weight of 30,000 Daltons, and then freeze-drying, egg yolk aqueous protein powder containing *H. pylori*-antibodies is obtained.

EXAMPLE 3

Measuring Antibody Value of Three Pathogenic Factors in Combination

A sample was formulated by combining 200 $\mu$g of urease; 400 $\mu$g of outer-membrane; and 400 $\mu$g of flagella, with an equal weight of oily adjuvant. 1 ml of this sample was injected into 30 week old white leghorn hens, and the level of antibodies stimulated were measured at various intervals over 14 weeks. The production of antibodies was measured by the Microtiter method. The results obtained are set forth in Table 2 below.

TABLE 2

| Period after injection (weeks) | Antibody value (measured by Microtiter) |
| --- | --- |
| 0 | >20 |
| 1 | 40 |
| 2 | 80 |
| 3 | 160 |
| 4 | 320 |
| 6 | 640 |
| 8 | 1280 |
| 10 | 1280 |
| 12 | 1280 |
| 14 | 640 |

As evident from the above, the antibody value reaches a maximum after about 8 weeks and diminishes after about 14 weeks.

EXAMPLE 4

The Inhibition Effect of H. pylori on the Production of Urease

The inhibition of urease production by the selected four active strains L. acidophilus HY2177 and HY2185, L casei HY2743 and L. plantarum HY2207 was determined as follows:

After cultivation of H. pylori for two days in brucella agar, the cells were washed twice with 20 mM (millimolar) phosphate buffered saline (pH 7.0) and sonicated for 6 min at 4° C. After centrufuging at 11,000 g for 10 min, the supernatant was used as a source of crude urease. Each lactic acid strain was cultivated in 12% skim milk for 24 hrs at 37° C. after inoculation of the seed culture ($10^6$ cfu/ml). Urease activity is determined by measuring the pH at 30 min intervals over a period of 2hrs to observe the change in pH. 800 μl of crude urease and 1.6 ml of cultivated lactic acid bacteria were added into a urea broth (13.6 ml) and adjusted to pH 6.5. FIG. 1 is a plot of pH as a function of time; it is seen that the pH is below about 6.8 for only two strains, L. acidophilus HY2177 an L. casei HY2743 indicating a strong inhibition effect on urease activity which is maintained after 90 min. Despite the excellent inhibition activity of in vitro inhibition of H. pylori growth, the pH of L. acidophilus HY2185 and L. plantarum HY2207 keeps rising even after 90 min when it reaches about pH 735. It is evident that excellent in vitro inhibition of H. pylori by a strain is not a measure of the strain's ability to inhibit urease production.

EXAMPLE 5

Effect of Active Strains on Inhibition of H. pylori Attachment to AGS Cells

A. Effect After Infection with H. pylori (Treatment Effect)

The effect on treated AGS cells, which are commercially grown gastric mucosal cells, after they were infection with H. pylori is measured as follows: AGS cells ($10^5$ cells/well) were added to five wells. $10^6$ H pylori cells were added to each well. A numerically greater number of H. pylori cells are used to facilitate binding to the AGS cells because the latter are much larger in size. The AGS cells and H. pylori cells are kept in contact with each other for 3 hr which allows enough time for the latter to bind to the AGS cells.

The AGS cells and H. pylori cells are then inoculated (10 μl of $1\times10^9$ cfu/ml) with each of the four active strains (identified in Example 4 above), which had been incubated in 12% NFMS solution for 24 hours at 37° C., one strain per well. Each active strain was delivered in RPMI 1640 (10% fetal bovine serum) to stimulate binding. After one hour, the cells were washed three times with distilled water using a plate shaker. After washing, 1 ml of sterile distilled water was added to the cells and allowed to stand for one hour. Cell pellets obtained from centrifuging were then added to urea broth (1 ml) and allowed to stand for 1 hr at 37° C., during which the H. pylori cells alone generate urease. By measuring turbidity as absorbance at 560 nm (nanometers) the number of H. pylori cells bound to the AGS cells is determined.

Figure 2:
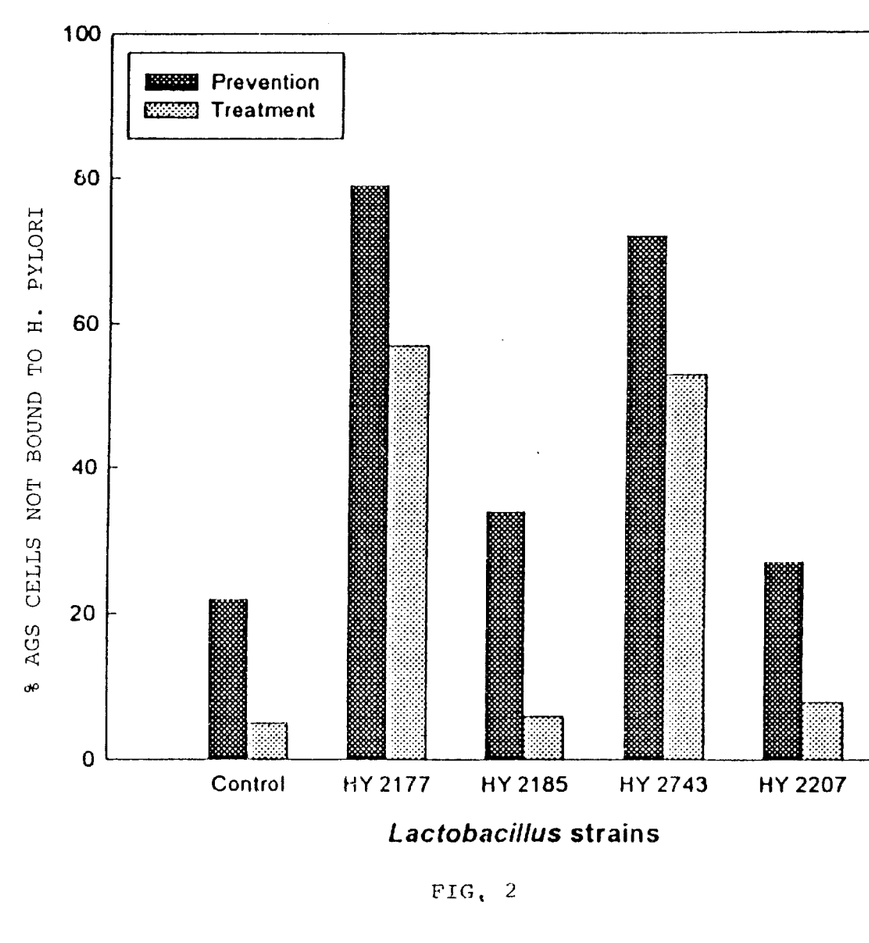
FIG. 2 shows five pairs of bars in a graph, one pair for the control and the others for Lactobacillus strains of acidophilus, casei, and plantarum visually depicting the inhibitory effect of each strain when administered to AGS cells prior to, and after, being infected and bound by *H. pylori*; the effect i shown as the percent of AGS cells which remain unbound to *H. pylori* cells.

For the control, 12% skim milk was used containing both AGS cells and H. pylori cells. Referring to FIG. 2 it is seen that the bar graph for the control indicates that, with no treatment with any lactobacillus after infection, only about 5% of the AGS cells are not bound to H. pylori cells; when treated with HY2177 and HY2743 nearly 60% and 50% respectively of the AGS cells remain unbound. Thus the inhibitory effect of L. acidophilus HY2177 and L. casei HY2743 is seen to be about ten-fold.

B. Effect of Treating with Lactobacillus Strains Prior to Infection with H. pylori (Preventive Effect)

For the measurement of the preventive effect AGS cells ($10^5$ cells/well) were added to five wells. Each of the four active strains (used in part A) with RPMI 1640 (10% FBS) were added to the wells, one strain per well, and 3 hr were allowed the cells in each strain to bind to the AGS cells. Thereafter, H. pylori ($10^6$ cells/well) was added to incite a reaction. After 1 hr the cells were washed 3 times with distilled water using a plate shaker. The control (for prevention) shown in FIG. 2 illustrates the effect on AGS cells in 12% skim milk after contact for 1 hr with H. pylori without prior treatment with an active strain. After washing, 1 ml sterile distilled water was added to the cells and allowed to stand for 1 hr and a cell pellet obtained from centrifuging was added to urea broth (1 ml) to measure attachment. Absorption at 560 nm was measured after 1 hr reaction at 37° C. The bar graphs indicate that, when the active strains are administered prior to infection, nearly 80% and 70% of the AGS cells remain unbound, when HY2177 and HY2743 respectively had been administered, while in the control only about 20% of the AGS cells remain unbound. Thus the inhibitory effect of L. acidophilus HY2177 and L. casei HY2743 is seen to be about four times better than when there is no prior treatment with an active strain.

EXAMPLE 6

Effect of Active Strains on Inhibition of Interleukin-8 (IL-8) Production

When H. pylori interacts with the mucous membrane, stimulation of a variety of cytokines occurs. The secretion of IL-8 as a result of infection with H. pylori, is the most significant. The IL-8-induced neutrophils or macrophages are a direct cause of gastritis. Because of this, inhibition of IL-8 production can be an important method for inhibiting the occurrence of gastritis. The inhibition effect of an active strain on the production of IL-8 is measured with an ELISA assay (Quantikdne® Human IL-8 Immunoassay kit, R&D Systems Europe Ltd.). Turbidity of cultures was standardized at the beginning. H. pylori, L. acidophilus HY2177, and L. casei HY2743 cells were each centrifuged at 9,000 rpm for 10 min at 4° C. H. pylori cells were washed with 10 ml of phosphate buffered saline. Cell pellets were standardized using 1 ml of commercially available Han's F12 medium and diluted by a ratio of 1:50. The turbidity was measured by absorbance at 660 nm.

Cell population=16.95×$A_{660}$×(dilution factor)×$10^8$/ml
H. pylori=1.084×16.95×50×$10^8$ =9.18×$10^8$
Lactobacillus=1.408×16.95×50×$10^8$ =11.93×$10^8$ Four duplicate groups of wells were prepared as shown below. For Group D, 100 μl of lactic acid bacteria which was adjusted to 7.5×$10^8$ cfu/ml and 100 μl of H. pylori adjusted to the same concentration were mixed. Samples were taken for ELISA Assay initially (at time zero), and then after 6, 12, 24, 36, and 48 hrs had elapsed.

A: Control
B. L. acidophilus HY2177 (or L. casei HY2743) treatment
C: H. pylori treatment
D: L. acidophilus HY2177 (or L. casei HY2743)+H. pylori treatment 1) Sampling After collecting the contents of each well, cells were centrifuged for 3 min at 12,000 rpm (4° C.). Supernatant liquid was stored at −70° C. for the assay.

2) Standard Solution

One liter stock solution (2,000 pg/ml, picograms per mililiter) was prepared by diluting 2 ml of RD5P (from the ELISA KIT) (5×) five-fold with distilled water. From this stock solution, 100 μl standard solution was made by two-fold dilution.

3) Assay

100 μl assay diluent (RDI-8 in the EUISA kit), 50 μl sample and standard solution were added to the plate well. After the addition of 100 μl conjugate solution, the plate was shaken for 2.5 hr at room temperature. The plate was then washed 6 times with 400 μl washing buffer and 200 μl of substrate solution made with reagents A and B in the assay kit (reagent A: reagent B=1:1). After 30 min of reaction, absorption at 492 nm was measured.

Figure 3:
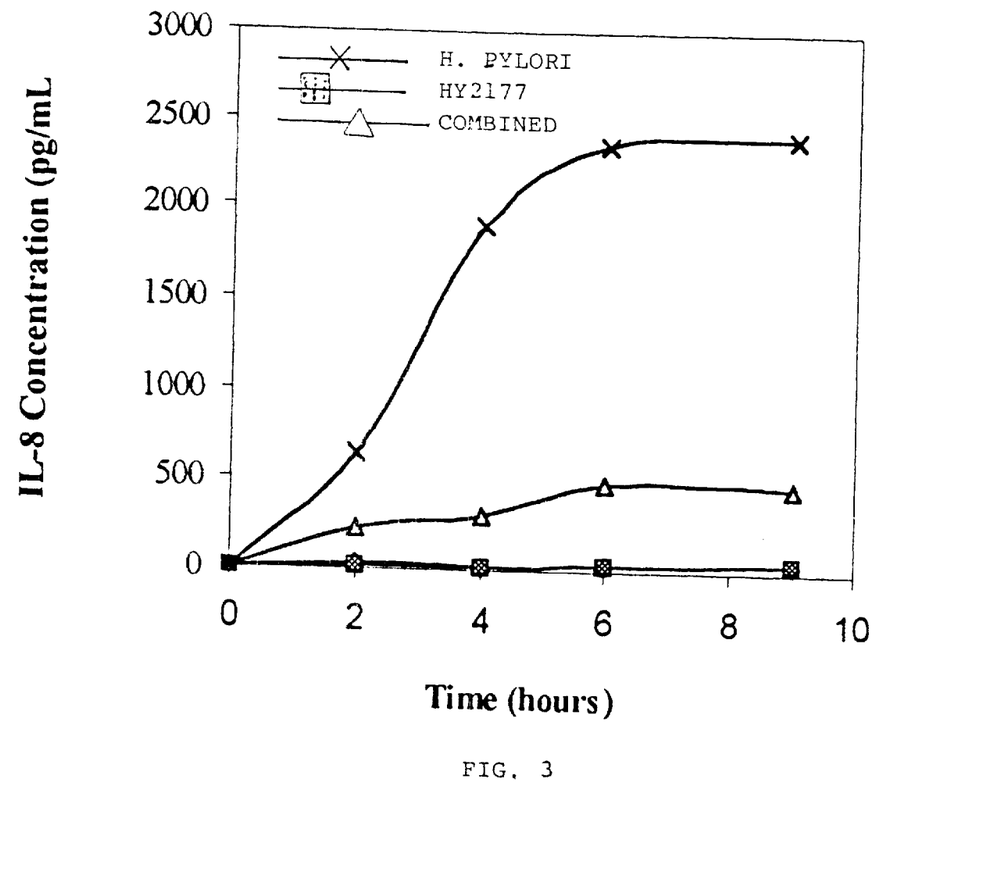
FIG. 3 shows three curves in a graph plotting the concentration of Interleukin-8 as a function of time, one each for *L. acidophilus* HY2177 and *H. pylori* respectively, and one for the combination of *L. acidophilus* HY2177 and *H. pylori*; the control with the active strain alone does not generate any IL-8.

The control showed no production of IL-8. As seen in FIG. 3 production of IL-8 was significantly reduced by the addition of HY2177 to H. pylori in the medium. Untreated, production of IL-8 by H. pylori reaches nearly 2500 pg/ml after 6 hr. The control group did not generate any IL-8, and the HY2177 culture did not generate a significant amount of IL-8. Treatment with L. acidophilus HY2177 decreases the effect of H. pylori allowing production of only about 300 pg/ml IL-8 after 6 hr, which is about an eight-fold decrease.

Figure 4:
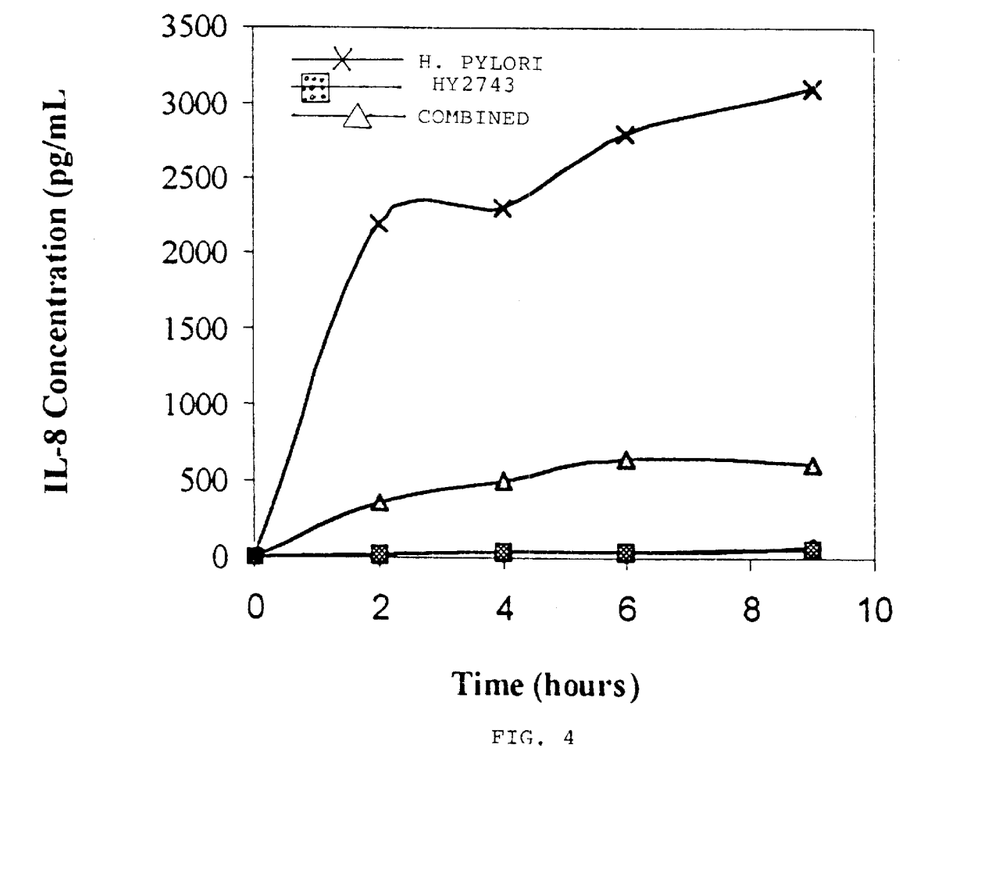
FIG. 4 shows three curves in a graph plotting the concentration of Interleukin-8 as a function of time, one each for *L. casei* HY2743 and *H. pylori* respectively, and one for the combination of *L. casei* HY2743 and *H. pylori*; the control with the active strain alone does not generate any IL-8.

As seen in FIG. 4 production of IL-8 was significantly reduced by the addition of HY2743 to H. pylori in the medium. Untreated, production of IL-8 by H. pylori reaches and exceeds 2500 pg/ml after 6 hr. Note that the values measured for H. pylori at different times produce curves which are not the same. Treatment with L. casei HY2743 allows production of only about 500 pg/ml of IL-8 after 6 hr, which is about a five-fold decrease.

EXAMPLE 7

Inhibition of the Effect of H. pylori by Treating Infected Mice

Four week old BALB/c mice are used which did not show any positive activity for urease. Three groups of the mice, 30 mice in each group, were placed in specific pathogen free conditions at 25° C. and 50% humidity. Mice in the control group (Group A, "negative") received no treatment with any Lactobacillus after being infected with 0.5 ml of 7.5% sodium bicarbonate buffer with H. pylori. The mice in each of the three Groups were treated with 1 ml of 2–4×$10^9$ cfu/ml of H. pylori in 75% sodium bicarbonate buffer, three times a day for two days, a total of six feedings. The mice were then fed their regular diets, three times/day, for six weeks. Mice in Groups B and C were then fed 2–5×$10^{10}$ cells of L. acidophilus HY2177 and L. casei HY2743 each day for 21 days. The mice in Group A were fed their regular diets and were left untreated. All the mice were sacrificed and their stomachs halved, one-half to be used to count the remaining number of H. pylori cells, and the other half to measure the amount of urease present. The control showed 100% infection both by cell count and by urease production.

TABLE 3

Effect of Treatment after Infection

| Strain | Infected mice | % cured |
|---|---|---|
| L. acidophilus HY2177 | 4/30 by cell count[1] | 87 |
| | 5/30 by urease conc.[2] | 83 |
| L. casei HY2743 | 5/30 by cell count[1] | 83 |
| | 7/30 by urease conc.[2] | 77 |

[1]Cell count: after removal of food remnants, the one-half portion of stomach membrane was dipped in brucella broth with 10% horse blood and homogenized. The homogenized material was diluted until spreadable without clumping, then spread onto a brucella agar plate for incubation. Plates were incubated for 5–7 days at 37° C. in a 10% $CO_2$ incubator for colony detection. The presence of any H. pylori colony forming unit indicates infection.
[2]Urease concentration: after removal of food remnants, the one-half portion of stomach membrane was washed with 10 ml of phosphate buffered saline and centrifuged. Cell pellets were dispersed in 1 ml of Han's F12 medium and diluted by a ratio of 1:50. The turbidity was measured by absorbance at 660 nm. Visible turbidity indicates infection.

EXAMPLE 8

Inhibition Effect of Active Strains when Ingested Prior to Infection by H. pylori (Preventive Effect)

Four week old BALB/c mice are used which did not show any positive activity for urease. Three groups of the mice, 30 mice in each group, were placed in specific pathogen-free conditions at 25° C. and 50% humidity. Mice in the control group (Group D, "negative") were fed 0.5 ml of 7.5% sodium bicarbonate buffer, three times a day for two days, a total of six feedings, and not infected with H. pylori. The mice in all three Groups D–F were fed 2–5×$10^{10}$ cells of L. acidophilus HY2177 and L. casei HY2743 each day for 14 days. Thereafter infection was incited by adding 1 ml of 2–4×$10^9$ cfu/ml of H. pylori in 7.5% sodium bicarbonate buffer, three times a day for two days, as to Groups E and F. The mice were the irregular diets, three times/day, for six weeks. All the mice were sacrificed and their stomachs halved, one-half to be used to count the remaining number of H. pylori cells, and the other half to measure the amount of urease present. The control showed no infection whether by cell count or by urease production.

TABLE 4

Effect of Treatment Prior to Infection

| Strain | Infected mice | % cured |
|---|---|---|
| L. acidophilus 2177 | 2/30 by cell count[1] | 93 |
| | 3/30 by urease conc.[2] | 90 |
| L. casei HY2743 | 3/30 by cell count[1] | 90 |
| | 3/30 by urease conc.[2] | 90 |

[1]Cell count: as in Table 3 above
[2]Urease concentration: as in Table 3 above

EXAMPLE 9

Effect of a Combination of L. Acidophilus 2177 and L. casei HY2743

0.1% of each culture, L. acidophilus HY2177 and L. casei HY2743, are inoculated into 12% skim milk for culture growth. Additionally, 0.05% of each culture are combined and inoculated into 12% skim milk. After 24–48 hr 170 μl of a solution of each of the grown cultures containing 1×10⁹ cfu/ml, is used to determine the zone of inhibition in a manner analogous to that described hereinabove for screening cultures for *H. pylori* inhibition. Three determinations are made and the average taken.

Figure 5:
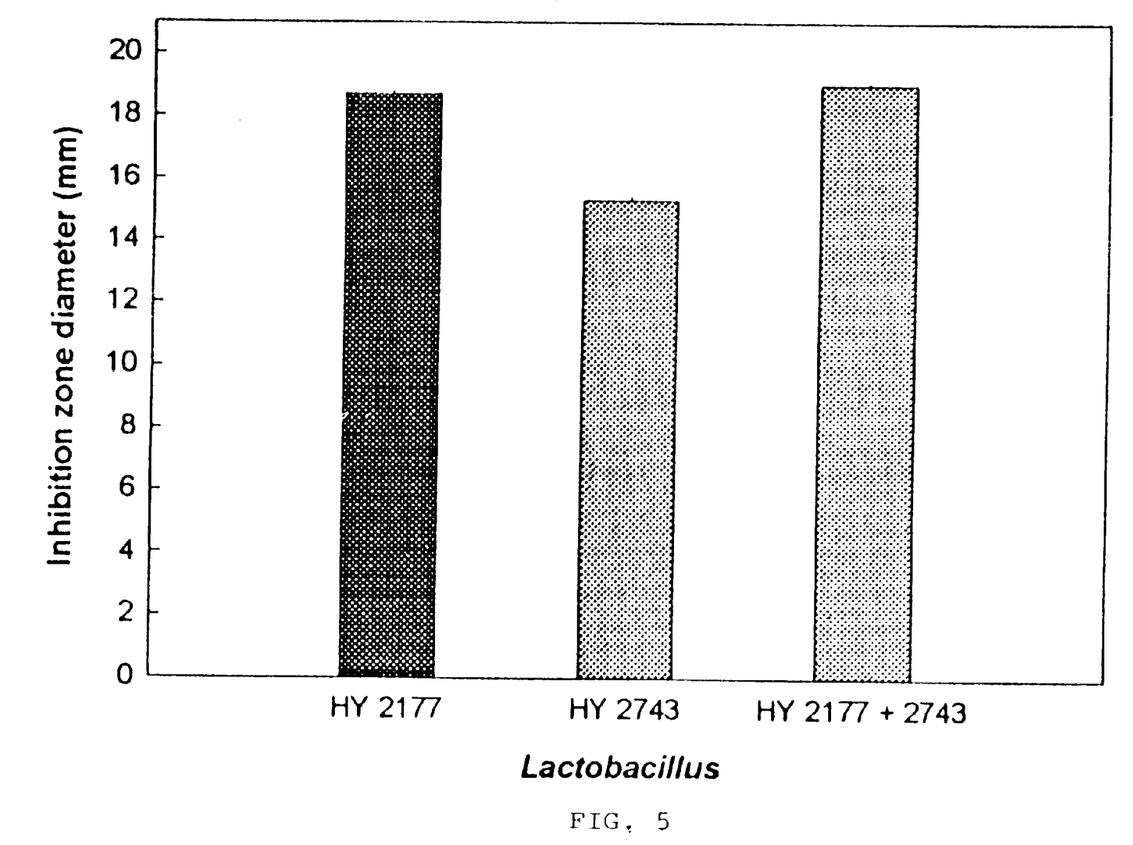
FIG. 5 shows three bar graphs two showing zones of inhibition generated by 0.1 ml of medium containing $10^7$ cfu/ml of each *L. casei* HY2743 and *L. acidophilus* HY2177, and the third showing a zone generated by a combination of 0.05 ml of medium of each of the cultures.

As seen in FIG. 5, *L. acidophilus* HY2177 and *L. casei* HY2743 generated zones of inhibition of 18.7±0.7 mm and 15.3±1.1 mm respectively. The zone of inhibition generated by the combination was 19.0±0.8 mm, indicating that the same number of cfu/ml of the combination is slightly more effective than the same number of cells of either culture by itself.

EXAMPLE 10

Manufacture of Fermented Milk using a combination of *L. acidophilus* HY2177 and *L. casei* HY2743

Reconstituted milk is prepared using 3–15% by weight non-fat milk solids in distilled water. The milk is then pasteurized using ultra-high temperature (UHT) at 135° C. for 3 sec. After cooling to 30° C. the milk is inoculated with 10⁶ cfu/ml of each culture and incubated until the pH reaches 4.5, indicating the milk is fermented.

Antibodies from egg yolk (0.1–10% weight) are then added. A syrup is prepared comprising the following ingredients in the ranges stated: fruit concentrates from 0.1–10 % weight, edible fibers from 0.5–5 % weight, fructose from 0.5–10 % weight, and the remaining amount as oligosaccharides. A minor proportion by weight of the syrup is mixed into fermented milk typically in a ratio of fermented milk to syrup in the range from about 10:1 to 10:4 depending upon the targeted market. Most preferably about 10 parts by weight of the syrup is mixed into 90 parts by weight of the fermented milk. After homogenization, the fermented milk/syrup product is packaged in individual containers. Evaluations of the product indicate that it is free of clumps, has excellent taste, flavor and texture, with mouth-feel which is comparable to that of the product which contains no added active strain.

EXAMPLE 11

Clinical Trial of the Combined Active Strains 40 humans, 31 male and 9 female having a mean age of about 34 years, who tested positive when they were screened for *H. pylori* infection using a urease breath test (UBT) were chosen. They were divided into a treatment group with 18 males and 3 females, and a placebo group with 13 males and 6 females. Each was given a UBT test a CLO (campylobacter like organism) test to corroborate the results of the UBT test. Also, cells were taken from the mucous cell membrane in the antrum of the stomach, before and after a 4-week treatment period to obtain a density analysis; in addition the foregoing tests were repeated on each individual on numerous occasions during the 4-week period. The treatment group is fed 400 ml of fermented milk (manufactured as described in Example 9) each day, in 100 ml portions; the placebo group received fermented milk with no active strains added.

In the following Table 5 is set forth the endoscopic findings for all 40 subjects 21 of whom were chosen for treatment with the active strains, and 19 of whom received no active strains. The findings were within the range expected for humans infected with *H. pylori*.

|  | Treatment | Placebo |
|---|---|---|
| Mean Age (years) | 33.7 | 33.5 |
| Sex Ratio (M:F) | 18:03 | 13:06 |
| Endoscopic Findings |  |  |
| Normal | 6 | 11 |
| Atrophic | 5 | 2 |
| Erosive | 7 | 3 |
| Others | 3 | 3 |
| Compliance | 96.60% | 94.20% |

After the 4-week period, the treatment group showed a 53% reduction in UBT values whereas in the placebo group, only a 26% reduction in UBT values was observed. For the treatment group, the changes in the UBT values were statistically significant (p=0.0072). The results are significant because of the relatively short period over which the subjects received the active strains.

The results from the CLO test after the 4-week period, indicate that 18 out of 21 test subjects showed a reduction in *H. pylori* populations while 3 out of 21 showed a negative response (no reduction, or an increase in populations) from the CLO test. As expected, all in the placebo group tested positive for *H. pylori*.

After the four-week trial period, 8 out of 21 subjects (38.1%) from the treatment group showed a reduction in density of *H. pylori* from the antrum. A 10.53% reduction in *H. pylori* density was observed from the control group indicating there was some overall improvement despite receiving no active strains.

EXAMPLE 12

Manufacture of the Active Strains in Powder-form

10⁶ cfu/ml of each culture, *L. acidophilus* HY2177 and *L. casei* HY2743, is inoculated in an optimum growth medium (MRS medium) and incubated for 18–24 hours at 37° C. under pH 5–6 control. Upon the completion of the fermentation process, the cultures are centrifuged at 10,000 g at 4° C. Cell concentrates are blended with 5% skim milk, 2.5% whey, and 5% sucrose before freeze-drying. Each culture contained 1×10¹¹ cfu/gram in powder form.

EXAMPLE 13

Manufacture of Health Food Containing Active Strains

Health food containing lactic acid bacteria is prepared using cultures prepared using the method shown above (Example 10). In this formula, 20% *L. acidophilus* HY2177 and *L. casei* HY2743 (by weight), 10% oligosaccharides, 20% glucose, 5% fructose, 2% vitamin C, 5% fruit flavoring, 5% aloe, 15% edible fiber, and 18% psyllium husk were blended. The finished product containing more than 5×10⁸ cfu/gram of the active strains is packaged in a pouch or bottle.

EXAMPLE 14

Mutine Adherence Inhibition Test

The prophylactic effectiveness of several samples were compared as follows: A culture of *H. pylori* (3×10⁴ cfu/ml) in broth was added to three 24 well plates each coated with 0.2% pig's stomach mucous membrane Mycine solution. To the wells of each plate was added 1 ml of the broth; then, to each plate was added 1 ml of each of three test samples A, B and C respectively, as follows:

Sample A=1 ml broth+1 ml of saline containing 1 mg of purified antibodies obtained in Example 2 (from outer-membrane+flagella)

Sample B=1 ml broth+1 ml of saline solution containing 1 mg of powdered commercially available spray-dried egg yolk containing whatever commonly present antibodies which are not destabilized.

Sample C (control)=1 ml broth+1 ml cow's serum albumen (BSA: 1 mg/ml)

After standing for 1 hour, all plates are washed with phosphate buffered saline and the number of live *H. pylori* was evaluated by measuring the urease they produced. The activity of urease was measured by the amount of ammonia produced per unit of time by the Indol-phenol method using the absorption at the wavelength of 557 nm. The results are presented in Table 5 below.

TABLE 5

| Sample identif. | number of live bacteria (%) |
|---|---|
| Sample A | 10 |
| Sample B | 90 |
| Sample C (control) | 100 |

EXAMPLE 15

Manufacture of Yogurt with Prophylactic Properties Against Gastritis, Duodenal and Gastric Ulcers A combination of the active strains *L. acidophilus* HY2177+*L. casei* HY2743 each present in about $5 \times 10^8$ cfu/ml, is added to freshly prepared yogurt, along with *H. pylori*-antibodies obtained from outer-membrane+flagella (as, in Example 2). Addition to acidic yogurt unexpectedly minimizes the loss of antibody activity by enzyme dissolution, at the same time providing nutrition and prophylactic and therapeutic properties.

The composition of the yogurt is as follows:

TABLE 6

Composition of Yogurt

| component | amount, % |
|---|---|
| cow's milk | 75.0 |
| powder cow's skim milk | 3.0 |
| fruit juice | 10.0 |
| liquid fruit sugar | 3.0 |
| hydrated crystal grape sugar | 4.0 |
| solid fruit sugar | 2.0 |
| distilled water | 3.0 |
| The yogart has a pH of about 4. | |

EXAMPLE 16

Comparative Prophylactic Effectiveness (in mice) of Various Combinations of lactic acid bacteria and *H. pylori*-antibodies which mice were infected after being fed with each sample below:

Sample 1: yogurt+*H. pylori*-antibodies (IgY) (outer-membrane+flagella) (see Example 2)

Sample 2: yogurt+both active strains ($5 \times 10^8$ cfu/ml each)

Sample 3: yogurt+*H. pylori*-antibodies (IgY)+both active strains ($5 \times 10^8$ cfu/ml each)

Control group: yogurt only

The samples were prepared in a manner analogous to that described in Example 10.

Mice (BALB/c), albinos 4 weeks old and disease free, with normal flora and no particular sensitization to *H. pylori*, were divided into 4 groups of 10 mice each. Each mouse in each group was fed 1 ml of a sample 3 times a day for 1 week along with their usual and regular diet. Group 1 was fed Sample 1; Group 2 was fed Sample 2; Group 3 was fed Sample 3; Group 4 was fed Sample 4. At the end of the week, the stomach of each mouse in each group was injected with 0.2 ml of a *H. pylori* KS 51 culture (about $5 \times 10^8$ cfu/ml) and the injection was repeated a total of three times over two days while the mice were continued to be fed as usual. The following day the mice were starved except for water. The mice were thereafter fed their regular diet along with the yogurt samples.

After 6 weeks, the mice were sacrificed and their stomachs washed with saline solution the absorption of which at 550 nm was measured (for each mouse) to determine the presence of urease; an absorption of 0.25 indicates presence of urease at low level. This level was used to determine remaining infection; that is, if absorption was less than 0.25 the mouse is deemed to have no live *H. pylori* cells. The number of mice out of 10 in each group, which showed an absorption of less than 0.25 (deemed free of infection) were then recorded.

Effective prevention is defined by a level of absorption <0.25. In the control group, fed only yogurt, as might be expected, all 10 mice showed an absorption above 0.25, and were infected. In the group fed IgY (sample 1), 5 out of 10 mice showed absorption <0.25 (infection-free); in the group fed both active strains (sample 2), 6 out of 10 mice were infection-free; in the group fed both active strains combined with IgY (sample 3), 8 out of 10 mice were infection-free. The effective prevention rate of Sample 3 (containing *H. pylori* antibodies and both active strains) is 33% better than that found for Sample 2 (containing both active strains, no *H. pylori* antibodies) which in turn is about 20% better than that found for Sample 1 (containing only *H. pylori* antibodies).

EXAMPLE 17

Comparative Effectiveness of Treatment (in mice) of Various Combinations of lactic acid bacteria and *H. pylori*-antibodies which mice were infected before being fed with each sample below:

The same Samples made up in Example 16 above are used, except that the mice are first infected and then fed to measure the extent to which such treatment may have eliminated evidence of infection.

As before, 4 weeks old mice (BALB/c) were used, and they were divided into the 4 groups, every mouse having been infected with *H. pylori* KS 51 (about $5 \times 10^8$ cfu/ml) by injection which was repeated a total of three times over two days. The mice were then fed with the various samples over a period of one week after which they were sacrificed, and their stomachs examined as before, for urease content, the level of absorption at 550 nm being the criterion (as before), namely, absorption had to be <0.25 before a mouse was deemed essentially free of infection.

In the control group, fed only yogurt, as might be expected, all 10 infected mice showed an absorption above 0.25. In the treatment group fed IgY (sample 1), 2 out of 10 mice were infection-free; in the group fed both active strains (sample 2), 4 out of 10 mice were infection-free; in the group fed both active strains combined with IgY (sample 3), 6 out of 10 mice were infection-free. The effective prevention rate of Sample 3 (containing *H. pylori* antibodies and both active strains) is 50% better than that found for Sample 2 (containing both active strains, no *H. pylori* antibodies) which in turn is about twice as good as that found for Sample 1 (containing only *H. pylori* antibodies).

EXAMPLE 18

The following is a recipe for a processed milk-drink comprising cow's milk and vegetable stabilizer containing the active strains & IgY as in Example 2 above:

TABLE 7

Recipe for Processed Milk-Drink

| Ingredient | Content, % by wt |
|---|---|
| Cow's Milk | 42.3 |
| Water | 49 to 50 |
| Egg yolk antibodies | 1 to 2 |
| Sugar | 6.5 |
| Pectin | 0.2 |
| Flavor | 0.001 |

EXAMPLE 19

The active strains may be used alone or in combination with IgY as in Example 2 above, to provide a solid health food supplement comprising a dosage amount of the active strains along with a non-active comestible carrier. The term "non-active comesitble carrier" refers to a food ingredient which has no measurable effect on the activity of the active strains and which food ingredient is typically used to provide desirable properties such as bulk, body and a pleasant mouth-feel. A non-active comestible carrier is commonly selected from a non-fermentable polysaccharide such as maltodextrin, polyfructose and the like; disaccharides such as lactose, sucrose, maltose and the like; a stabilizer such as pectin, gelatin, gums, carboxy-methyl-cellulose and the like; a vegetable stabilizer including a source of fiber such as vegetable fiber (cellulose), beta-glucan, and grain fibers such as those from oats and barley; and fermented milk powder. The following is a typical recipe for the solid health food supplement:

TABLE 8

Recipe for health food supplement

| Ingredient | Content, % by wt |
|---|---|
| Fermented milk powder[1] | 42.3 |
| Maltodextrin | 57.7 to 58 |
| Vegetable fiber | 10 |
| Sugar | 3.5 |
| Egg yolk antibodies | 1 to 2 |
| High fructose corn syrup | 6.5 |
| Pectin | 2.0 |
| Flavor | 0.001 |

[1]prepared as in Example 10 above

The ingredients are blended and freeze dried to obtain a powder which is either put into capsules or made into tablets containing a dosage amount of the active strains, typically at least $1 \times 10^8$ cfu/gm.

We claim:

1. A food for general human consumption, comprising a food stored at a temperature in the range from about $-45°$ C. but no more than $45°$ C., and effective to inhibit and/or prevent the growth of *Helicobacter pylori* in a human stomach, said food being fortified with an amount effective to inhibit and/or prevent the growth of *Helicobacter pylori*, of an active strain of a non-toxic living microorganism selected from the group consisting of *Lactobacillus acidophilus* HY2177, and *Lactobacillus casei* HY2743, said strain by itself being effective against *H. pylori* not only in vitro but also in vivo.

2. The food of claim 1 including in addition an amount of antibodies having a Microtiter antibody titer in the range from about 30 to about 200, said antibodies being obtained in the yolk of an egg of a hen immunized against a pathogenic factor identified as urease of *H. pylori*.

3. The food of claim 1 including in addition an amount of antibodies having a Microtiter antibody titer in the range from about 30 to about 200, said antibodies being obtained from the yolk of an egg of a hen immunized against a pathogenic factor identified as flagella of *H. pylori* and outer membrane of *H. pylori* separated from the rest of the *H. pylori* cells.

4. The food of claim 2 selected from the group consisting of a conventional food of lactic acid origin and a non-conventional food, said conventional food being selected from the group consisting of yogurt, buttermilk cream cheese and ice cream, said non-conventional food being a nutritional yogurt drink.

5. The food of claim 4 wherein said conventional food is yogurt.

6. The food of claim 4 wherein said non-conventional food is a drinkable nutritional yogurt-like or milk-drink supplement.

7. The food of claim 4 wherein said non-conventional food is a health food supplement comprising fermented milk powder and vegetable stabilizer.

8. The food of claim 4 wherein said antibodies are obtained from the yolk of an egg of a hen immunized against a pathogenic factor identified as a combination of urease of *H. pylori* and outer membrane of *H. pylori* separated from the rest of *H. pylori* cells.

9. A solid health food supplement effective to inhibit and/or prevent the growth of *Helicobacter pylori* in a human stomach, said solid health food supplement comprising a non-active comestible carrier and a dosage amount of an active strain of a non-toxic living microorganism selected from the group consisting of *Lactobacillus acidophilus* HY2177, and *Lactobacillus casei* HY2743, said strain by itself being effective against *H. pylori* not only in vitro but also in vivo .

10. A method of preventing and/or treating disorders associated with infection by *Helicobacter pylori*, said method comprising, administering to a human a nutritional food in combination with an active strain of a living microorganism in an amount effective to inhibit or prevent the growth of *H. pylori* in a human stomach, said living microorganism being selected from the group consisting of *Lactobacillus acidophilus* HY2177 and *Lactobacillus casei* HY2743 served in plural servings spaced apart by a period in the range from 1 hour to 3 days.

11. The method of claim 10 wherein said food includes an amount of antibodies having a Microtiter antibody titer in the range from about 30 to about 200, said antibodies being obtained from the yolk of an egg of a hen immunized against a pathogenic factor identified as urease of *H. pylori*.

12. The method of claim 10 wherein said food includes an amount of antibodies having a Microtiter antibody titer in the range from about 30 to about 200, said antibodies being obtained from the yolk of an egg of a hen immunized against a pathogenic factor identified as flagella of *H. pylori* and outer membrane of *H. pylori* separated from the rest of the *H. pylori* cells.

13. The method of claim 10 wherein said food is selected from the group consisting of a conventional food of lactic acid origin and a non-conventional food, said conventional food being selected from the group consisting of yogurt, buttermilk, cream cheese and ice cream, said non-conventional food being a nutritional yogurt drink.

14. The method of claim 13 wherein said conventional food is yogurt.

15. The method of claim 12 wherein said antibodies are obtained from the yolk of an egg of a hen immunized against a pathogenic factor identified as a combination of urease of *H. pylori* and outer membrane of *H. pylori* separated from the rest of *H. pylori* cells.

16. The method of claim 13 wherein said non-conventional food is a nutritional yogurt-like or milk-drink supplement.

17. The method of claim 13 wherein said non-conventional food is a health food supplement comprising fermented milk powder and vegetable stabilizer.

18. A method of preventing and/or treating disorders associated with infection by Helicobacter pylori, said method comprising, administering to a human a solid health food supplement effective to inhibit and/or prevent the growth of *Helicobacter pylori* in a human stomach, said solid health food supplement comprising a non-active comestible carrier and a dosage amount of an active strain of a non-toxic living microorganism selected from the group consisting of *Lactobacillus acidophilus* HY2177, and *Lactobacillus casei* HY2743, said strain by itself being effective against *H. pylori* not only in vitro but also in vivo, said solid health food supplement served in plural servings spaced apart by a period in the range from 1 hour to 3 days.

* * * * *